United States Patent
Tillman et al.

(10) Patent No.: US 12,016,767 B2
(45) Date of Patent: Jun. 25, 2024

(54) ELECTROMAGNETIC SYSTEM FOR RAPID CANNULATION OF FENESTRATED ENDOVASCULAR GRAFTS

(71) Applicant: University of Pittsburgh—Of the Commonwealth System of Higher Education, Pittsburgh, PA (US)

(72) Inventors: Bryan W. Tillman, Allison Park, PA (US); Catherine C. Go, Pittsburgh, PA (US); Youngjae Chun, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 314 days.

(21) Appl. No.: 16/957,846

(22) PCT Filed: Jan. 8, 2019

(86) PCT No.: PCT/US2019/012693
§ 371 (c)(1),
(2) Date: Jun. 25, 2020

(87) PCT Pub. No.: WO2019/139898
PCT Pub. Date: Jul. 18, 2019

(65) Prior Publication Data
US 2021/0052363 A1    Feb. 25, 2021

Related U.S. Application Data

(60) Provisional application No. 62/615,311, filed on Jan. 9, 2018.

(51) Int. Cl.
*A61F 2/07*      (2013.01)
*A61M 25/09*     (2006.01)
*A61F 2/06*      (2013.01)

(52) U.S. Cl.
CPC ............... *A61F 2/07* (2013.01); *A61M 25/09* (2013.01); *A61F 2002/061* (2013.01); *A61F 2210/009* (2013.01); *A61M 2025/09175* (2013.01)

(58) Field of Classification Search
CPC .................. A61F 2/07; A61F 2002/061; A61F 2210/009; A61F 2250/0001; A61F 2/06; A61M 25/09; A61M 2025/09175
See application file for complete search history.

(56) References Cited

U.S. PATENT DOCUMENTS 6,401,723 B1 *  6/2002  Garibaldi .......... A61M 25/0127
                                                          128/899
8,945,202 B2 *  2/2015  Mayberry ............... A61F 2/856
                                                          623/1.13
(Continued)

FOREIGN PATENT DOCUMENTS

EP         1943974       7/2008
KR      2008-0031929     4/2008
WO      WO 2010/120548   10/2010

OTHER PUBLICATIONS

International Search Report and Written Opinion for related International Application No. PCT/US2019/012693, 11 pages, dated May 5, 2019.

*Primary Examiner* — Kelly J Bekker
*Assistant Examiner* — Andrew P. Restaino
(74) *Attorney, Agent, or Firm* — Klarquist Sparkman, LLP

(57) ABSTRACT

Disclosed are implantable tubular devices having a fenestration in a wall of the tubular device and a conductive coil positioned around the fenestration, such that the coil is operable to generate a magnetic field when electrical current flows through the coil. The magnetic field can be used to draw a ferrous or magnetically tipped guidewire or other (Continued)

device to and through the fenestration. In the example of a fenestrated endovascular graft, the coil can be used to draw a guidewire out through a fenestration into a branch blood vessel, such that the guidewire can be used to deliver a branch of the graft through the fenestration into the branch vessel. A power source can be contained in a nosecone.

9 Claims, 11 Drawing Sheets

(56) References Cited

U.S. PATENT DOCUMENTS

| | | | |
|---|---|---|---|
| 10,485,684 B2 * | 11/2019 | Marmur | A61F 2/07 |
| 2003/0014063 A1 * | 1/2003 | Houser | A61B 17/11 |
| | | | 606/153 |
| 2005/0154444 A1 * | 7/2005 | Quadri | A61F 2/07 |
| | | | 623/1.13 |
| 2008/0147173 A1 * | 6/2008 | Mciff | A61B 34/20 |
| | | | 623/1.34 |
| 2008/0167704 A1 * | 7/2008 | Wright | A61F 2/954 |
| | | | 623/1.23 |
| 2009/0005851 A1 * | 1/2009 | Pamoukian | A61F 2/954 |
| | | | 606/108 |
| 2009/0259296 A1 * | 10/2009 | McIff | A61B 6/12 |
| | | | 623/1.34 |
| 2011/0196397 A1 | 8/2011 | Frantz et al. | |
| 2017/0143938 A1 * | 5/2017 | Ogle | A61B 17/22 |
| 2019/0167407 A1 * | 6/2019 | Schaer | A61B 17/0401 |

* cited by examiner

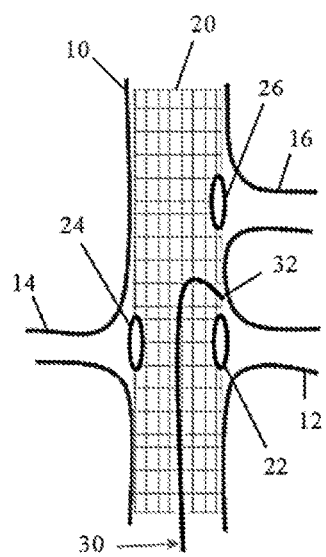 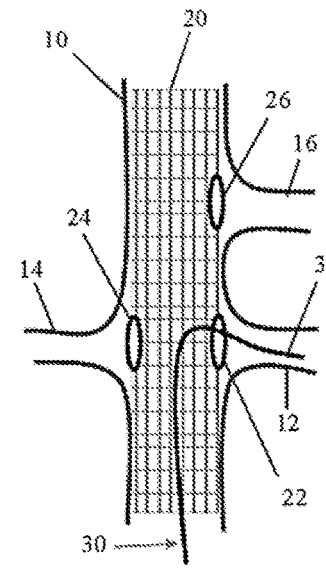 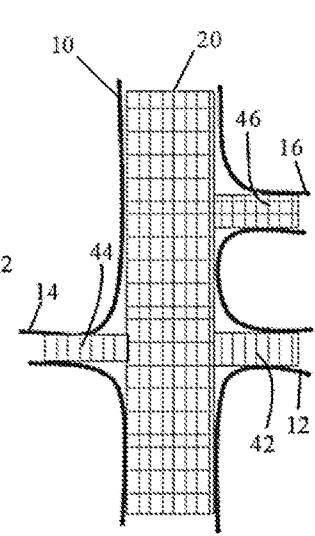
FIG. 1A  FIG. 1B  FIG. 1C
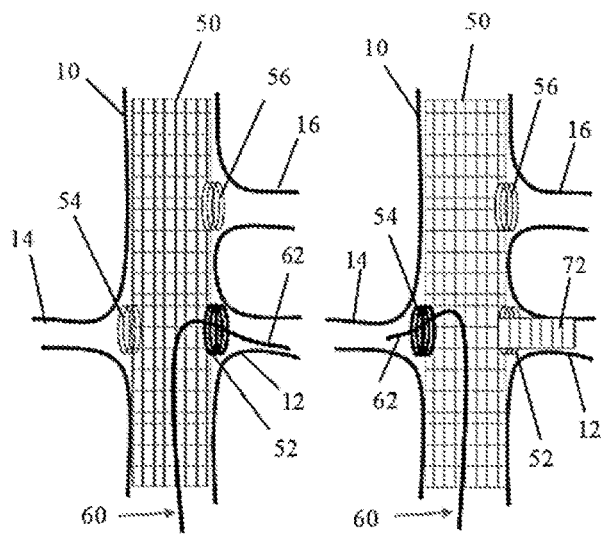 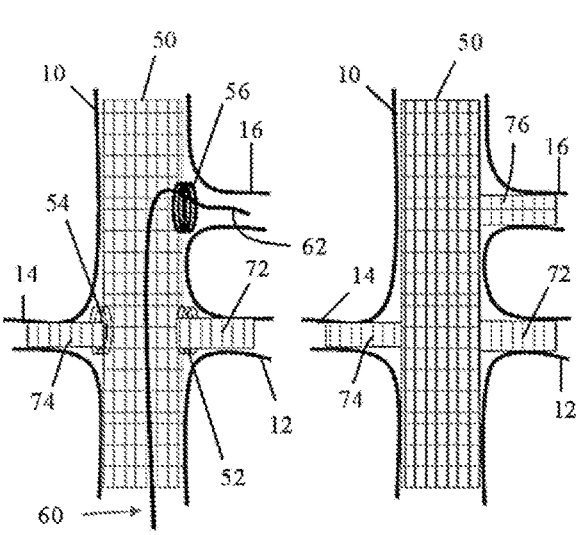
FIG. 2A  FIG. 2B  FIG. 2C  FIG. 2D

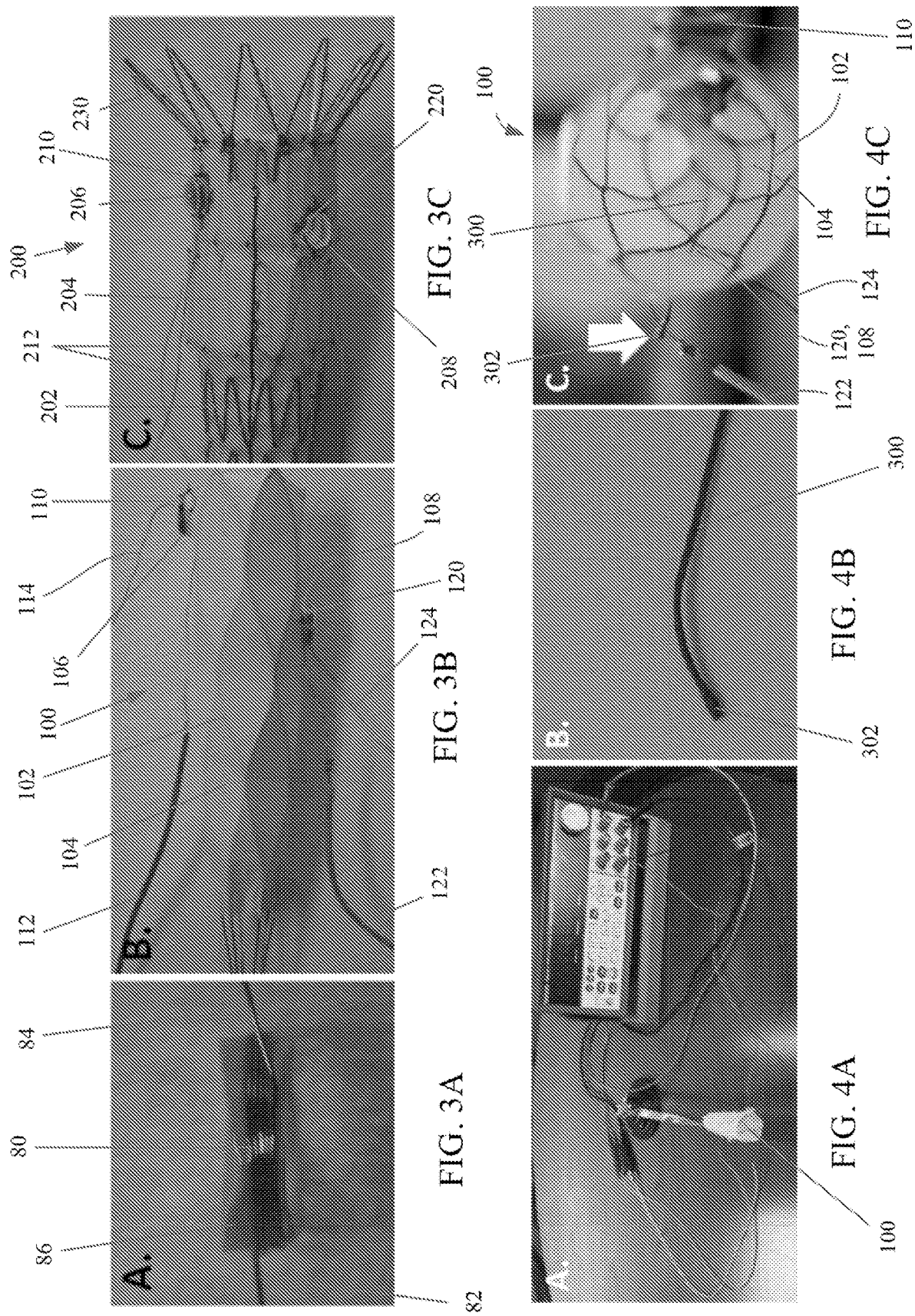

ELECTROMAGNETIC SYSTEM FOR RAPID CANNULATION OF FENESTRATED ENDOVASCULAR GRAFTS

CROSS-REFERENCE TO RELATED APPLICATIONS

This application is the U.S. National Stage of International Application No. PCT/US2019/012693, filed Jan. 8, 2019, which claims the benefit of U.S. Provisional Application No. 62/615,311 filed Jan. 9, 2018, which is incorporated by reference herein in its entirety.

FIELD

This application relates to medical devices, such as fenestrated endovascular stents or grafts, and to methods for operating and implanting such devices.

BACKGROUND

Grafts are often used to repair aneurysms, include aortic aneurysms. In the case of aortic aneurysm treatment, bifurcated grafts require cannulation of the iliac arteries. In more complex situations, a fenestrated graft may be used when the graft is positioned over arterial branches of the aorta, such as the renal or visceral (bowel) arteries. Fenestrations in the graft provide openings for blood to flow from the aorta, through the graft, and into the arterial branches. In some cases, the fenestrated graft can include stented "branches" that extend outward from a main tubular portion of the graft and into the arterial branches. Typically, the main tubular body of an aortic graft is implanted in the aorta first, and then each of the branches is delivered through the main tubular body, through fenestrations in the tubular body, and placed into the arterial branches extending from fenestrations radially outwardly.

However, it can be very difficult and time consuming to cannulate each of the fenestrations with a guidewire in order to place the stented branches. This difficult and time consuming process can expose patients to excessive radiation, pose other health risks for the patient, and consume more time of the medical staff performing the operation. Accordingly, there is a need in the art for devices and methods that can provide a simpler, more rapid, and safer implantation of the branches of these fenestrated implants.

SUMMARY

Disclosed herein are implantable devices having at least one fenestration in a wall of the device and a conductive coil positioned around the fenestration, such that the coil is operable to generate a magnetic field when electrical current flows through the coil. The magnetic field can be used to draw a guidewire or other device to and/or through the fenestration. In the example of a fenestrated endovascular graft, the coil can be used to draw a guidewire out through a fenestration into a branch blood vessel (e.g., a renal artery), such that the guidewire can be used to deliver a branch of the graft through the fenestration into the branch vessel. The use of electromagnetic forces to quickly and accurately guide a metallic guidewire tip into and through the fenestrations can greatly improve the safety and efficacy of the implantation procedure. The use of an electromagnet, in particular, allows one of several coils to be selectively magnetized to specifically direct cannulation to one of multiple fenestrations.

The disclosed technology includes any tubular or partially-tubular body such as an endovascular graft or stent, or other non-tubular body that is placed within a vessel or other conduit in the body, that is configured to be implanted within a patient and includes at least one fenestration in the body, such as in a sidewall, and further includes a coil positioned around the fenestration, the coil being operable to generate a magnetic field when electrical current flows through the coil. In some embodiments, the device can be implanted within a blood vessel to treat an aneurysm of the blood vessel. At least one fenestration can be positioned such that, when implanted a main conduit or chamber, the fenestration aligns with a branch of a main conduit or chamber, so that fluid can flow between the main conduit/chamber and the branch conduit through the fenestration.

The device can include any number of fenestrations and corresponding coils. Each coil can be individually activated with electrical current to generate its own magnetic field. Each magnetic field, when activated, can draw a guidewire tip, catheter tip, or other transvascular device to and/or through the corresponding fenestration from within the main body of the device. Each coil can include its own pair of electrical leads that are coupled to a power source. The leads can comprise structural components of the main body, such as wires or segments of a metallic stent frame. Thus, these parts of the device can serve a dual purpose of providing structure to the stent (e.g., to hold the walls of the anatomical vessel in place) and providing an electrical conduit to carry electrical current through the coils. The coils and the leads can be electrically insulated.

In some embodiments, the coils are electrically coupled to an external power source via wires extending though the vasculature and/or through a catheter. In some embodiments, the device can include a removeable power source (battery) or transcutaneous induction charger operable to generate electrical current through the coil.

In some embodiments, a plurality of coils can be coupled to an electrical switch configured to determine which of the first and second coils is activated with an electrical current. A person can manually operate the switch outside the patient to determine which coil is active at what time. A first coil can be activated to cannulate a first vessel branch, and then the first coil can be deactivated and a second coil can be activated to cannulate a second vessel branch, and so on.

The disclosed technology also includes methods, including any method comprising positioning a first device within a patient, the first device including a coil positioned around an opening in the first device; positioning a second device within the patient adjacent to the opening in the first device; and causing electrical current to flow through the coil to create a magnetic field that draws the second device to the opening in the first device. The first device may comprise any implanted device, such as any of the devices disclosed herein. The second device can include any transluminal device that can pass within the first device, such as a guidewire or catheter. Causing electrical current to flow through the coil can include creating a magnetic field that draws the second device through the opening in the first device and into an adjacent anatomical structure, such as a branch vessel. The methods can further comprise delivering a third device through the opening in the first device over or through the second device. The third device can include a stent branch or other implant component that is to be placed in the adjacent anatomical structure.

The foregoing and other objects, features, and advantages of the disclosed technology will become more apparent from the following detailed description, which proceeds with reference to the accompanying figures.

BRIEF DESCRIPTION OF THE DRAWINGS

FIGS. 1A-1C illustrate a process for implanting branches of a fenestrated endovascular graft using a guidewire to cannulate each fenestration. As used herein, a fenestration includes any hole, opening, or passageway passing through a wall in a device. In FIG. 1A, a main body of the graft is implanted and a guidewire is manually directed into the main body. The operator probes around with the guidewire tip until a fenestration is found. In FIG. 1B, the guidewire is passed through a fenestration in the main body of the graft into a branch vessel. FIG. 1C shows three stented braches having been implanted using the guidewire.

FIGS. 2A-2D illustrate a process for implanting branches of a fenestrated endovascular graft using electromagnetic forces to guide the guidewire into the fenestrations. In FIG. 2A, electrical current is applied a first coiled wire positioned around a first fenestration to create a magnetic force that draws the tip of the guidewire to and through the first fenestration. In FIG. 2B, after a first stented branch has been placed, the process is repeated with a second coiled wire positioned around a second fenestration. In FIG. 2C, the process is repeated with a third coiled wire positioned around a third fenestration. FIG. 2D shows three stented braches having been implanted using the method of FIGS. 1A-1C.

FIG. 3A shows an exemplary coiled wire.

FIG. 3B shows an exemplary custom fenestrated endovascular graft with two coiled wires positioned around two fenestrations.

FIG. 3C shows a modified fenestrated endovascular graft with two coiled wires positioned around two fenestrations. This device includes a flared stent structure at one end, such as could be positioned in a vascular chamber or enlarged vessel portion.

FIG. 4A shows an exemplary fenestrated endovascular graft having coiled wired around the fenestrations and with the coiled wires coupled to an electrical controller for experimental validation testing.

FIG. 4B shows an exemplary guide wire with a metallic tip that is magnetically attractive.

FIG. 4C shows the result of a successful test where a guidewire has been magnetically drawn out through a fenestration (arrow) via an electrically activated coiled wire position around the fenestration.

In FIG. 13A, the branch angles posteriorly, and as shown in FIG. 13B, further advancement of a probing wire can dislodge both the probing wire and the wire's catheter/sheath (green).

In FIG. 15A, the magnetically tipped sheath engages a fenestration opening of the stent using magnetic attraction. The probing wire can then be advanced from the sheath into the branch artery. FIG. 15B illustrates how the magnetic coupling between the sheath tip and the fenestration allows the sheath to pivot or rotate without losing the magnetic connection, which can provide a desirable angle to better access the branch vessel with a probing wire and avoid dislodgement.

DETAILED DESCRIPTION

Figure 5:
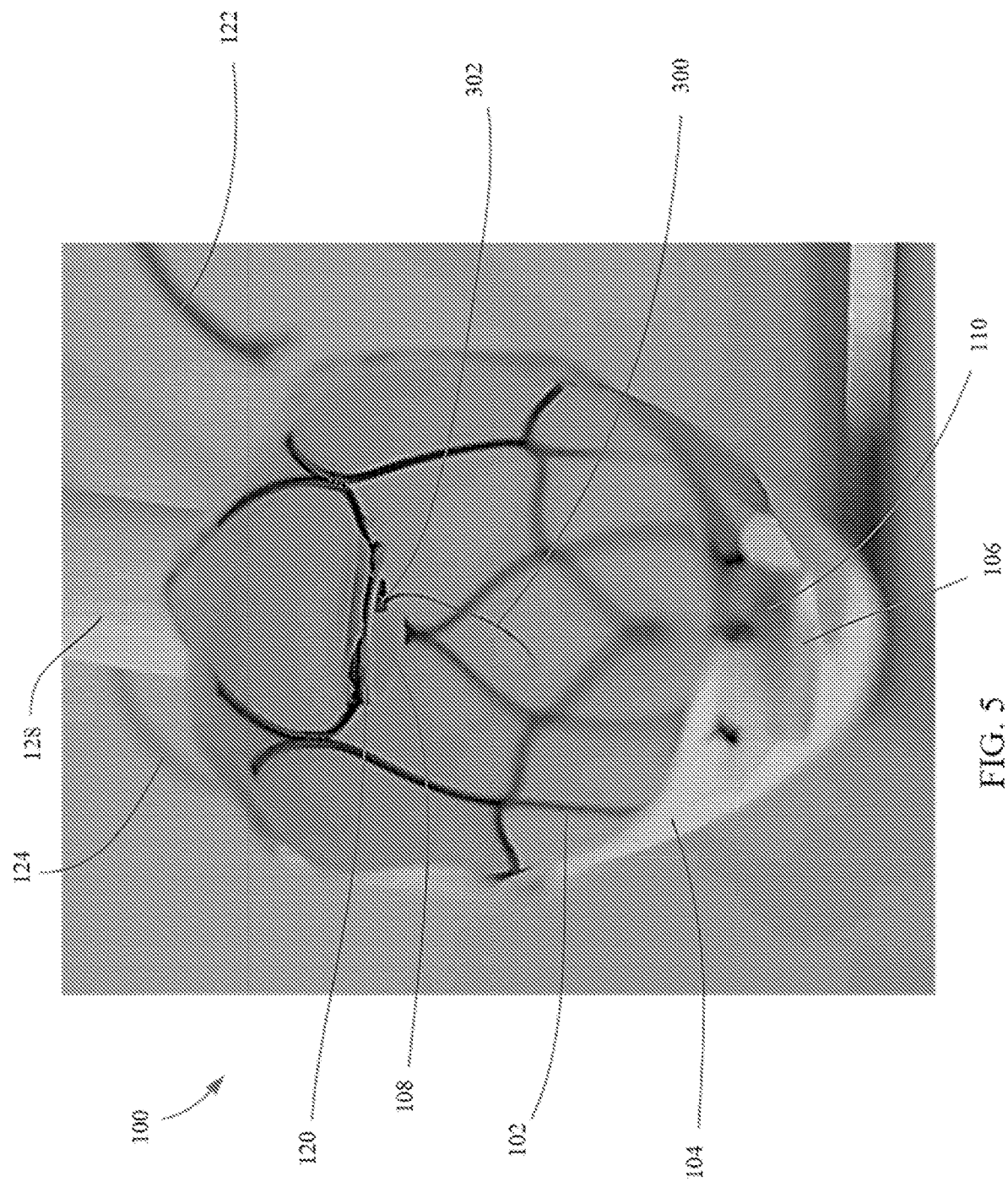
FIG. 5 is a view into a stented graft showing the inside of a fenestration with a coiled wire positioned around it. A guidewire with a metallic tip has been drawn into the fenestration by magnetic force created by electrical current flowing through the coiled wire.

Stent grafts can be used to treat weakened blood vessels and other tubular structures in the body. Stent grafts can provide rigidity and structure to maintain a vessel in an open, operative shape. Sometimes stent grafts can be used to treat aneurysms in vessels, such as aortic aneurysms (e.g., in the abdominal aorta or in the aortic arch). In other applications, stented grafts can be used to open occluded or collapsed vessels, or vessels damaged by trauma or other causes. In other applications, stented grafts can be implanted in conduit structures other than blood vessels, such as within the heart, endocrine ducts and other ducts, respiratory passages (e.g., trachea, bronchi, nasal passages), spinal canal and other nervous conduits, esophagus, intestines, urinary tract, reproductive conduits, etc. The disclosed technology is broadly applicable for use in connection to any such anatomical conduit or related application.

In some cases, a stented graft can be positioned in a section of a vessel that includes smaller vessel branches extending away from the main vessel. In such cases, a fenestrated graft can be used, including fenestrations in the graft that align with the smaller vessel branches. This allows for blood or other fluid to flow through the smaller vessel branches without unnecessary impediment from the implanted device. For example, to treat an aneurysm in the abdominal aorta, a fenestrated graft may be placed along a portion of the abdominal aorta that include the connections of the renal arteries. Such a fenestrated stent can include fenestrations that match the locations of the renal arteries so the fenestrations align with the renal arteries when implanted. Similarly, to treat an aneurysm in the aortic arch, a fenestrated graft may be placed along a portion of the aortic arch that includes the connections of the subclavian arteries, carotid arteries, and/or coronary arteries. Such a fenestrated stent can include fenestrations that match the locations of these branch arteries so the fenestrations align with the branch arteries when implanted. Other arteries that can be accommodated with this technology include the iliac arteries and superior mesenteric arteries. The disclosed technology is not limited to use in arteries, and can be used in veins, heart chambers, and in other anatomical ducts. In some methods, the locations of the fenestrations can be determined based on a CT scan or other imaging of a specific patient.

In some embodiments, a fenestrated graft can also include stent branches that extend from the fenestrations in the main tubular body of the graft a short distance outwardly from the main tubular body. These stent branches can be positioned in the smaller vessel branches when the device is fully implanted. However, the process for placing these stent branches can be very challenging and dangerous for the patient.

FIGS. 1A-1C illustrate an exemplary process for placing three stent branches. A section of an exemplary major vessel 10 is shown including three smaller vessel branches 12, 14, 16 extending laterally away from the major vessel 10. In FIG. 1A, the main body of an exemplary fenestrated graft 20 is shown already positioned within the major vessel 10, with fenestrations 22, 24, 26 aligned with the vessel branches 12, 14, 16. In FIG. 1A, a guidewire 30 has been introduced into the inside of the graft 20, but the tip 32 of the guidewire has missed the fenestrations and is poking into the wall of the device, which can cause damage or injury. In order to place the stent branches (see branches 42, 44, 46 shown in FIG. 1C), the tip 32 of the guidewire 30 must first be guided through the fenestrations 22, 24, 24 (one at a time) so that vessel branches can be cannulated and the stent branches can be delivered and implanted. In some methods, the guidewire is manipulated manually while the operator looks at an imaging monitor to visualize the location of the tip of the guidewire within body. In some methods, the operator "probes around" with the tip of the guidewire until the tip is successfully placed through one of the fenestrations and into one of the vessel branches. This can be time consuming and increase exposure of the patient to risks of radiation and vascular contrast. FIG. 1B shows an example when the guidewire tip 32 has been successfully placed through the fenestration 22 into the vessel branch 12.

The process of trying to manually place a guidewire (or other device) through a fenestration in a graft and into a vessel branch can be very time consuming, difficult, and risky. One challenge is using a 2D imaging modality such as X-ray imaging. The operator has limited vision of the true position of the guidewire tip and sometimes has to "probe around" with tip trying to get it through the desired fenestration. Not only is it difficult to guide a guidewire in a 3D space using a 2D imaging modality, but prolonged X-ray or other imaging can expose the patient to unsafe levels of radiation (e.g., cancer risk) and/or contrast use (e.g., renal failure). The medical staff may also be exposed to excessive radiation. Further, patients are kept in surgery longer and medical staff is required to spend more time when they could otherwise being treating others.

Once the guidewire 30 is successfully placed through the fenestration 22, the stent branch 42 can be delivered into the vessel branch using one or more cannulation devices that pass over the guidewire, using the guidewire to guide it into the vessel branch. This process can then be repeated to place stent branch 44 into vessel branch 14 and stent branch 46 into vessel branch 16 (as shown in FIG. 1C).

FIGS. 2A-2D show an exemplary method for placing stent branches using electromagnetic forces to guide the tip of the guidewire into each of the fenestrations, making the process faster and safer. The same exemplary major vessel 10 is shown including the three smaller vessel branches 12, 14, 16 extending laterally away from the major vessel 10. However, in this example, an exemplary fenestrated stent graft 50 is used. The graft 50 includes three fenestrations including coiled wires, or coils, 52, 54, 56 positioned around the openings. Each coil can be independently controlled to selectively apply electrical current to the coils, one at a time. At the same time, a guidewire 60 is used that includes a magnetically attractive tip 62 (e.g., made with a permanent magnet or alternately, a ferrous metal material).

In FIG. 2A, electrical current is applied to the coil 52, causing a magnetic field that draws the guidewire tip 62 through the coil and out into the vessel branch 12. A stent branch 72 can then be placed in the vessel branch 12 using the guidewire 60, as shown in place in FIG. 2B.

In FIG. 2B the coil 52 is deactivated (no electrical current) and a second coil 54 is activated (current applied), causing a magnetic field that draws the guidewire tip 62 through the coil 54 and out into the vessel branch 14. A stent branch 74 can then be placed in the vessel branch 14 using the guidewire 60, as shown in place in FIG. 2C.

In FIG. 2C the coil 54 is deactivated and a third coil 56 is activated, causing a magnetic field that draws the guidewire tip 62 through the coil 56 and out into the vessel branch 16. A stent branch 76 can then be placed in the vessel branch 16 using the guidewire 60, as shown in place in FIG. 2D. In FIG. 2D, all the stent branches are placed, the coils are deactivated, and the guidewire is removed.

The disclosed methods can further include the use of medical imaging technologies to assist in the implantation of the disclosed devices. Exemplary imaging modalities can include any combination of X-ray, computed tomography (CT), ultrasound, MRI, endoscopy, etc.

FIG. 3A shows an exemplary wire coil 80 that can be used with the disclosed technology. The coil 80 includes two wire ends, or electrical leads, 82 and 84 that can be coupled to an electrical current source. The coil shown in FIG. 3A includes several turns of wire. In any embodiment disclosed herein, a coil can include any number of turns, such as at least one turn, at least two turns, or more. More turns can create a stronger magnetic field, but can be more bulky. The direction of the coil turns and the direction of the current in the coil can determine the directionality of the magnetic field within the coil. In most cases, it can be desired to create a magnetic field that draws a metallic guidewire tip, or the like, radially outwardly through the fenestration and through the coil, out from within the tubular device. In some cases, the direction can be reversed to cause opposite motion.

In FIG. 3A, the coil 80 is positioned on a short fenestration stent "gate" portion 86, which can be attached to an opening in the side of a main stent body, as shown in FIG. 3B. This is just one example of the structure the herein disclosed wire coils can have. In other embodiments, the coils can include any number of windings, include just a single loop or multiple winding. The coils can comprise any electrically conductive material, such as copper, gold, etc. The coils can be coupled to the main stent body and/or graft in any matter, such as via sutures, adhesives, welds, etc, and/or can be integral portions of the main stent body. In some embodiments, the coils can be formed integrally with wires that make up the main stent body of the graft. Similarly, the wires that connect the coils to an electrical source can be integrated with the rest of the main stent body.

FIG. 3B shows an exemplary fenestrated stent graft 100 that comprises a main stent body 102 (e.g., a collapsible and expandable lattice of wires forming a generally cylindrical shape), a fabric covering 104 coupled to the main stent body, a first fenestration 106 including a first wire coil 110, and a second fenestration 108 including a second wire coil 120. The first wire coil 110 has leads 112 and 114 coupled to an electrical source and the second wire coil 120 can leads 122, 124 coupled to an electrical source. In this example, the leads are distinct from and extending away from the main stent body for ease of testing the device.

FIG. 3C shows another exemplary modified fenestrated stent graft 200 that comprises a main stent body 202 (e.g., a collapsible and expandable lattice of wires forming a generally cylindrical shape), a fabric covering 204 coupled to the main stent body, a first fenestration 206 including a first wire coil 210, and a second fenestration 208 including a second wire coil 220. The first wire coil 210 has leads 212 that can be coupled to an electrical source, as does the second wire coil 220. In this example, the graft also includes a flared stent end portion 230 that can be used to retain the device in a certain anatomical location, such as with the flared end 230 in an enlarged chamber.

The tubular devices disclosed herein, including devices 100 and 200, can comprise radially collapsible and expandable transvascularly deliverable devices. These devices may be radially compressed to a small diameter for delivery within a catheter or similar device through a patient's vasculature. For example, the delivery device can be inserted through the skin into a femoral artery and then be guided up through the femoral artery into the abdominal aorta for delivery of an aortic graft. At or near the implant location, the delivery device can uncover the implant and the implant can either self-expand radially due to elastic properties, or can be radially expanded using an inflated balloon or other expansion device. In other embodiments, the implanted devices may be delivery percutaneously, via minimally invasive surgery, or via open surgery. To aid in the radial expansion and compression, the device can include a structure frame or stent that forms a lattice shape or other geometrical configuration that allows for deformation to increase and decrease its circumferential dimension. Fabric material can be coupled to the stented portion to occlude openings in the frame, except that fenestrations and other portions may be left uncovered to allow fluid flow therethrough. The disclosed coils can be part of the stent frame, attached to the stent frame, or otherwise coupled to the device adjacent to the fenestrations.

FIG. 4A shows the graft 100 coupled to an electrical source that can apply selective currents through coils to test the device. FIG. 4B shows a distal end portion of an exemplary guidewire 300 having a tip 302 comprising a magnet and/or a material that is affected by magnetic forces (e.g., permanent magnet, electromagnet, or ferrous material). The distal end of the guidewire 300 can include a slight bend to help facilitate guiding the tip 302 of guidewire 300 through the fenestrations/coils. FIG. 4C shows the result of a successful test where the guidewire tip 302 has been magnetically drawn out through the fenestration 108 in the graft 100 via the electrically activated coiled wire 120 (not visible in FIG. 4C) position around the fenestration.

FIG. 5 is a view into an end of the graft 100 showing the inside of the fenestration 108 with the coiled wire 120 positioned around it. The permanent magnet (e.g. neodymium) or alternately, a ferrous, tip 302 of exemplary testing guidewire 300 is being drawn into the fenestration by a magnetic field created by electrical current flowing through the coiled wire 120.

Figure 7:
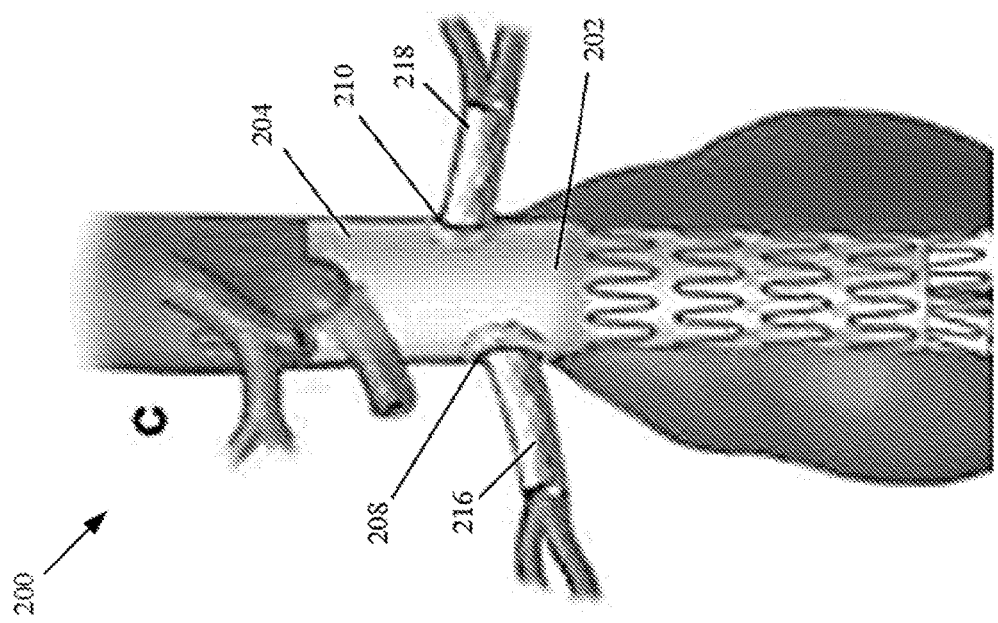
FIG. 7 shows the graft of FIG. 6 fully implanted.
Figure 6:
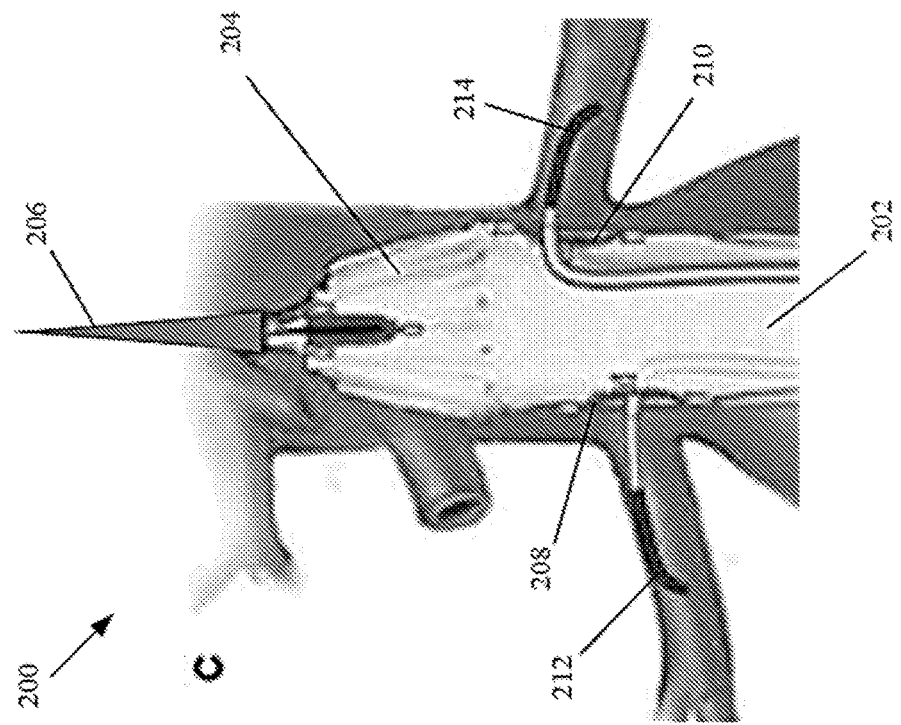
FIG. 6 shows another exemplary fenestrated endovascular graft being implanted, with an example nosecone (blue triangle) as a potential location for a portable power source.
Figure 9:
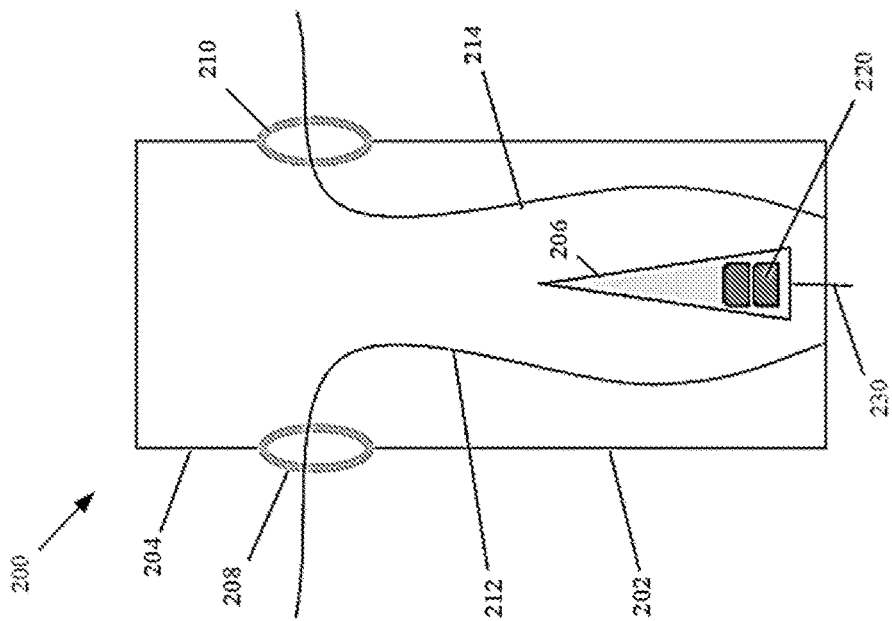
FIG. 9 is a schematic representation of the graft of FIG. 6 at a later stage of deployment, showing the nosecone being retracted.
Figure 8:
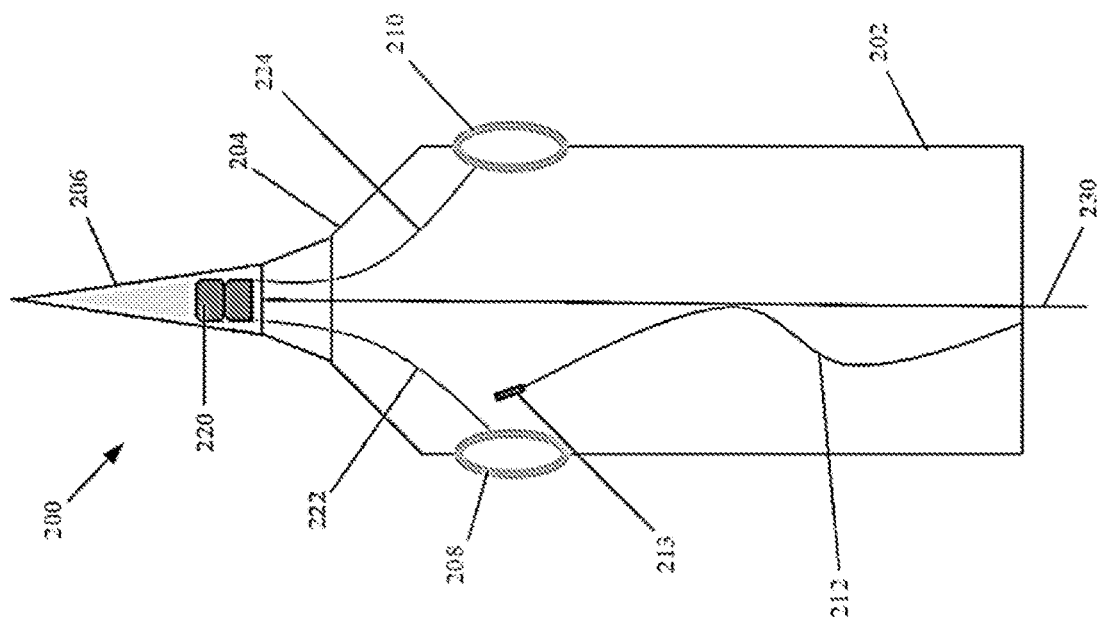
FIG. 8 is a schematic representation of the graft FIG. 6 partially deployed, showing a power source in the nosecone electrically coupled to the two coils.

FIGS. 6-8 illustrate alternative embodiments 200 that include a power source in a nosecone of the delivery device to supply electrical current to the coils. The graft 200 includes a main stent body 200 having a distal portion 204 and a nosecone 206 at the distal end, with coils 208 and 210 positioned around lateral openings that align with branch vessels. The power source, such as a battery, can be positioned in the nosecone 206, for example. FIGS. 8 and 9 show an example where a battery 220 in the nosecone 206 is coupled to the coils 208, 210 via wires 222, 224. The wires can run through or along the walls of the graft and/or can double as structural members of the stent. In FIG. 6, the coils 208, 210 are shown with guidewires 212, 214 having already been inserted through the coils (the same guidewire can be used to cannulate both in succession) using the generated magnetic field via the power source.

After the graft 200 is delivered to the desired portion of the anatomy, the proximal portion including the coils can initially be expanded, with the distal portion 204 still radially constrained, as shown in FIG. 6. From there, the branch vessels can be cannulated with guidewires, using the powered coils 208, 210, as shown in FIG. 6. From the position of FIG. 6, the nosecone 206 and power source 220 can be detached and withdrawn. For example, wires in the distal portion 204 of the stent can be coupled to the nosecone 206 during delivery, and then detached from the nosecone after the coils no longer need to be energized by the power source to generate magnetic fields. For example, a trigger wire 230 coupled to the nosecone can be used to detach the nosecone from the distal portion 204. When detached from the nosecone, the distal portion 204 of the graft can expand open to the position shown in FIGS. 7 and 9. Then, using the wire 230 or another wire attached to the nosecone, the nosecone 206 can be pulled out through the graft, as shown in FIG. 9, and out of the body.

Either before or after the nosecone 206 is retracted, the branch stent portions 216, 218 can be deployed over the guidewire and through the coils into the branch vessels, as shown in FIG. 7. Removing the nosecone first can provide more room to deliver the stent branches.

In alternative embodiments, a power source can be located embedded in the graft, or in another component that is detached and removable from the graft, such as at a proximal end of the stent.

In some embodiments, the magnetic field created by an activated coil can draw objects other that a guidewire tip to and/or through a fenestration. For example, a catheter or other transvascular device can include a magnetically attractive tip that can be attracted by an activated coil. The tip of such a catheter or sheath can include either a permanent magnet (e.g. neodymium) or ferrous component.

In some embodiments, the wire coils and the wires coupling the coils to a power source can be electrically insulated to prevent a short circuit. For example, the coils/wires can be individually coated with a polymeric material or other insulating material.

In some embodiments, the coils can be electrically coupled to a power source using wires that are also structural parts of the stent frame of the graft. Since the stent frame is typically already comprised of metallic strands, one or more of these metallic strands can be used also to conduct electrical current through a coil around a fenestration. For example, an electrical power source can be located in the nosecone (as in embodiment 200 above), or outside of the patient with two electrical leads extending through an insertion site in the patient and through a catheter to the graft being implanted. In the latter example, the two leads can be coupled to a proximal end of the main stent body at two different locations, one location being electrically coupled to one end of the wire coil and a second location being electrically coupled to the other end of the wire coil.

To facilitate coupling the coils to a power source, the stent frame can be made with two electrically conductive wire pathways extending axially from one end of the stent to the coil, and other parts of the stent can be made with non-conductive materials. In other embodiments, lead wires can extend from the two ends of the coil along the side of the stent frame to an end of the stent, or to wherever the power source is located.

In some embodiments, a battery or other power source can be positioned inside the patient adjacent to the graft, or as part of the graft itself, or as part of the delivery apparatus. This can remove the need to have wires running through the patient's vasculature to an external power source. In some embodiments, such a power source can remain in the body as part of the implant, while in other embodiments the power source can be removed during implantation or after the graft is implanted. In some embodiments, the power source can be part of the graft delivery device. In some embodiments, the power source can comprise a transcutaneous induction charger, such that an external device can be placed near the outside of the patient in the area of the implant and the coils in the graft within the patient can be supplied with electrical current via induction.

In some embodiments, each of the wire coils included in a graft can be individually controlled, such that each coil can be turned on and off as desired. The power source may include a switch that allows a user to select which coil to activate and which to deactivate. In this way, each of the coils can be activated one at a time so each can be sequentially cannulated without interfering with each other.

In some embodiments, the coils can be collapsible along with the rest of the graft to create a smaller overall profile during transvascular delivery. The coils can be non-circular, such as oval or almond shaped or polygonal, to assist with collapsing the coils. The coils can comprise materials that are electrically conductive and also resiliently deformable so that they can recover a desired shape after the graft is expanded at the implantation site within the body.

In some embodiments, the coils can comprise or be replaced with a permanent magnet. In some embodiments, the coils can comprise or be replaced with a simple metal loop that is not electrically energized, relying on a magnet at the tip of the guidewire instead.

In some embodiments, the guidewire can include a magnet at its tip, rather than or in addition to a ferrous metal. In some embodiments, the tip of the guidewire can comprise an electromagnet that is controllable between active and de-active states. In the active state, the tip of the guidewire is magnetic and is drawn to either another magnet or just a ferrous metal positioned around the fenestrations. In the de-active state, the guidewire can be released and redirected for later guidance toward another fenestration. In some embodiments, the tip of the guidewire can comprise a permanent magnet and the coils can be electrically activatable.

Figure 11:
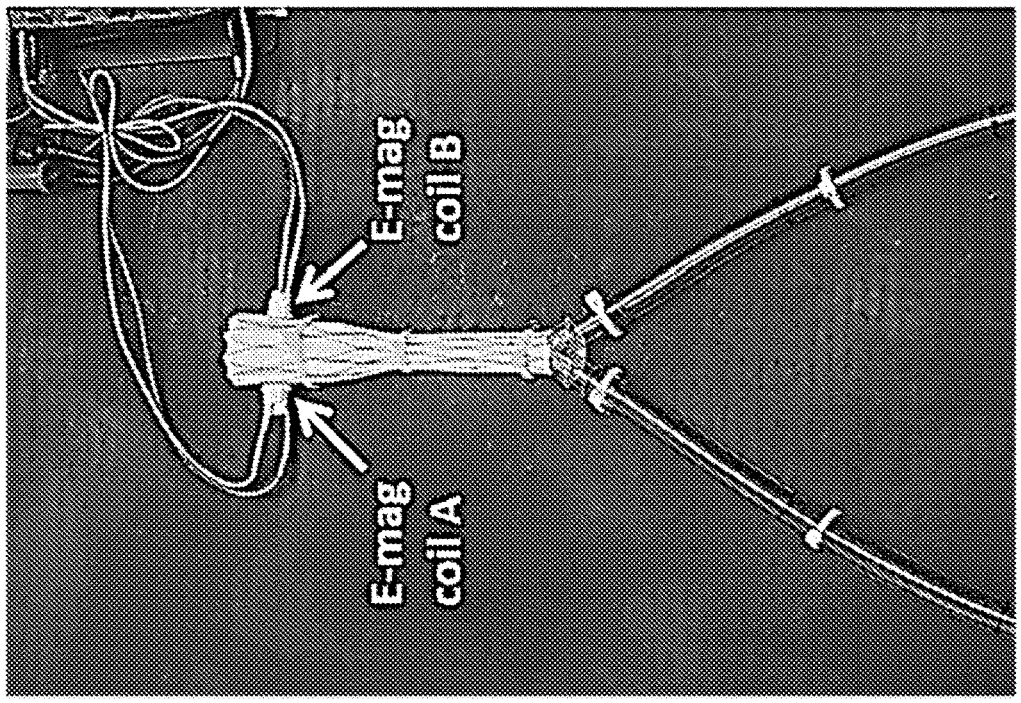
FIG. 11 shows an exemplary fenestrated stent with two electromagnetic fenestration coils electrically coupled to a power source/controller with wires.
Figure 10:
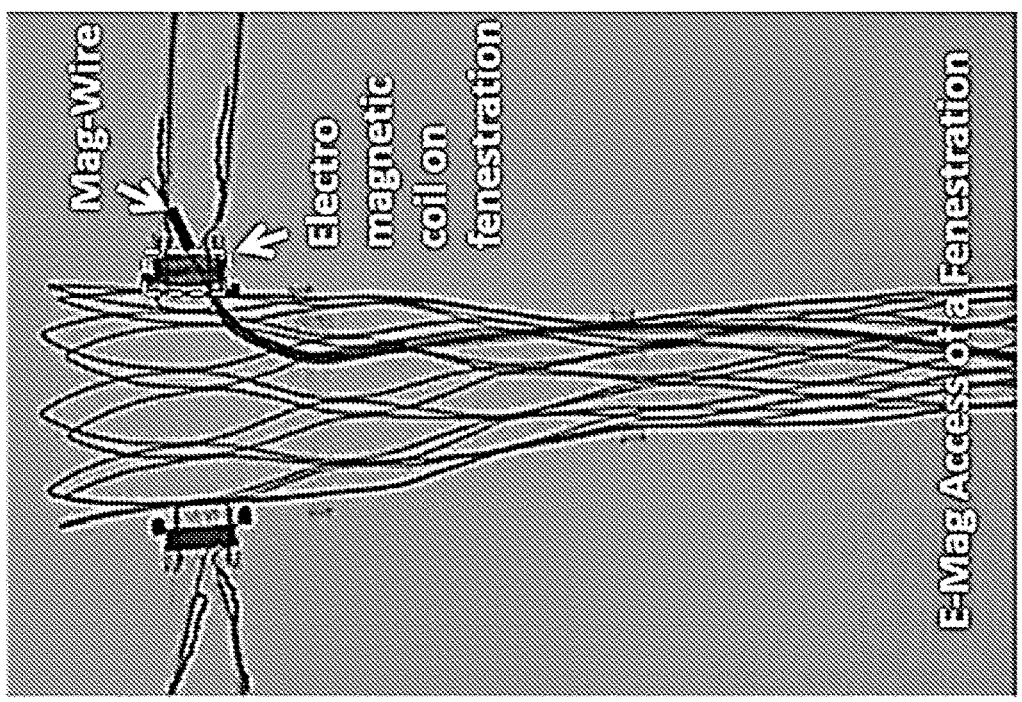
FIG. 10 is a fluoroscopic image of an exemplary magnetic wire cannulating an exemplary electromagnetic fenestration.

FIG. 10 is a fluoroscopic image of an example of a fenestrated stent with a magnetic guidewire (mag-wire) cannulating an electromagnetic coil at a fenestration. FIG. 11 shows the fenestrated stent of FIG. 10 in a simulated vascular environment with its two electromagnetic fenestration coils electrically coupled to a power source/controller with wires. In this example, the stent was fabricated with laser welded 0.155 nitinol wire and polytetrafluoroethylene with two renal artery fenestrations to mimic a fenestrated aortic endograft. The fenestrations are encircled with copper wire to create the coils, which are energized using a DC power supply to create a local electromagnetic field. Current was delivered at 4 amps to one fenestration at a time to magnetize each of the coils. A mag-wire was constructed from a neodymium magnet affixed to the end of a standard 0.035 Glidewire. A mock aortoiliac system was created with the custom stent and bifurcated ⅜-inch tubing to represent tortuous iliac arteries. Imaging was completed on a fixed fluoroscopic imaging unit (as exemplified in FIG. 10). In one experiment, the magnetic field created at each fenestration averaged 1.5 Gauss. Within the aortic model, the mag-wire was attracted only to the fenestration being energized. Five surgical clinicians of varying experience were each given 4 attempts with both a standard Glidewire and the illustrated electromagnetic system, with their time to completion recorded in seconds. The average time to cannulation with the Glidewire was 34.37±39.91 seconds, while the average time using the electromagnetic system was 5.73±2.67 seconds ($P<0.01$). There were no significant differences between vascular training levels using the electromagnetic system. The results of this study indicate that an electromagnetic system, as disclosed herein, can significantly enhance cannulation of fenestrations, for example in a complex endovascular aneurysm repair. This reduction in time to cannulation can significantly reduce radiation exposure time for the patient during the cannulation process.

Figure 12:
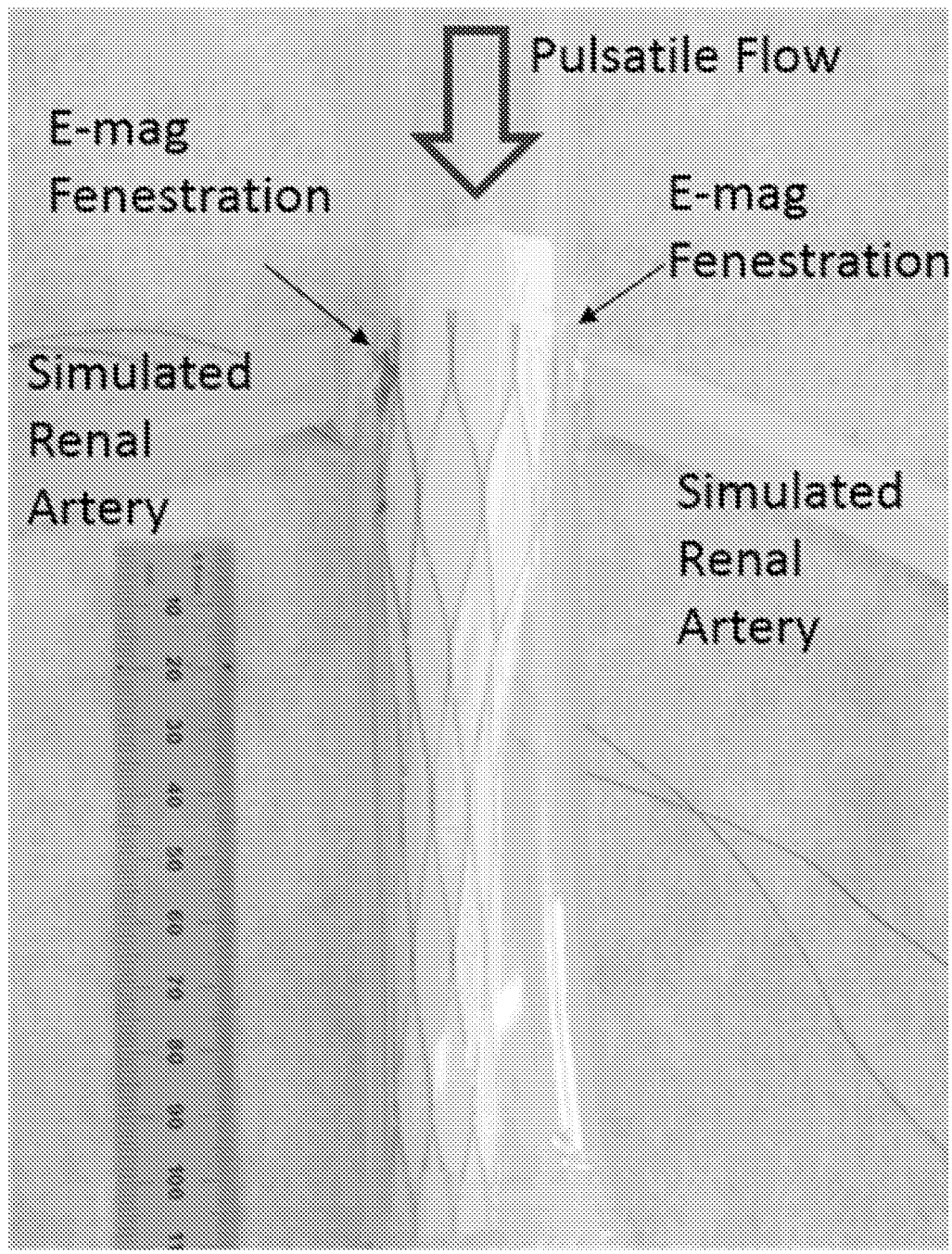
FIG. 12 shows an exemplary fenestrated stent having two electromagnetic fenestrations for the renal arteries, and illustrates how the technology can enhance cannulation of the stent branches even amidst pulsatile flow.

FIG. 12 shows an exemplary fenestrated stent having two fenestrations for the renal arteries with electromagnetic coils at the fenestrations, with the stent in a simulated aortic environment undergoing a pulsatile blood flow. This simulation demonstrated the efficiency of the herein disclosed technology to enhance cannulation of the stent branches even amidst pulsatile flow.

Figures 13A, 13B:
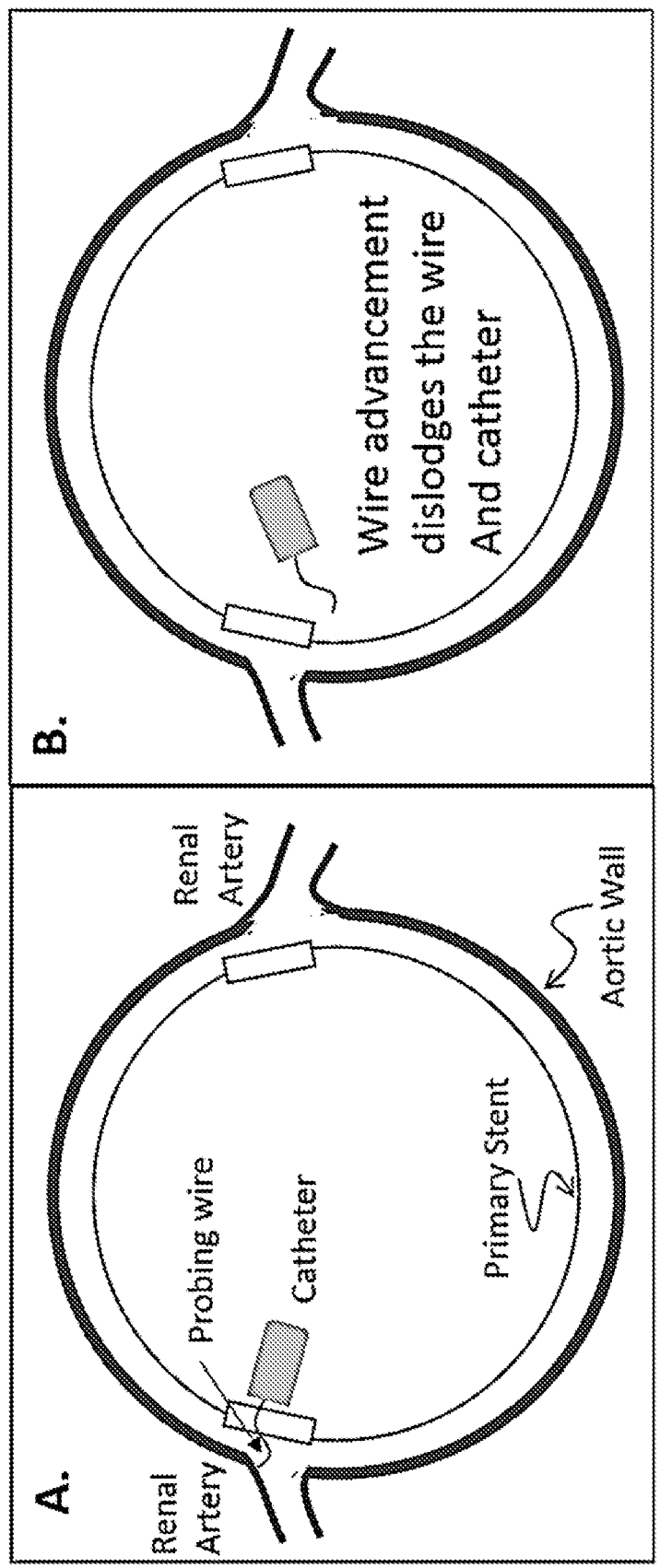
FIGS. 13A and 13B show cross-sectional views of the aorta with a fenestrated aortic stent positioned within, and illustrate a challenge of implanting fenestrated aortic stents.

FIGS. 13A and 13B show cross-sectional views of the aorta at the renal arteries with a fenestrated aortic stent positioned within, and illustrate a challenge of implanting fenestrated aortic stents at this location. As shown in FIG. 13A, the renal branches angle posteriorly from the aorta, making it difficult to direct a guidewire from a catheter/sheath within the primary stent into the renal branches. Due to the posterior angle of the posterior renal branches, the tip of the probing wire tends to get stuck on the side anterior wall of the renal branches, as illustrated. As shown in FIG. 13B, in this situation, further advancement of the probing wire can dislodge both the probing wire and the wire's catheter/sheath.

Figure 14A:
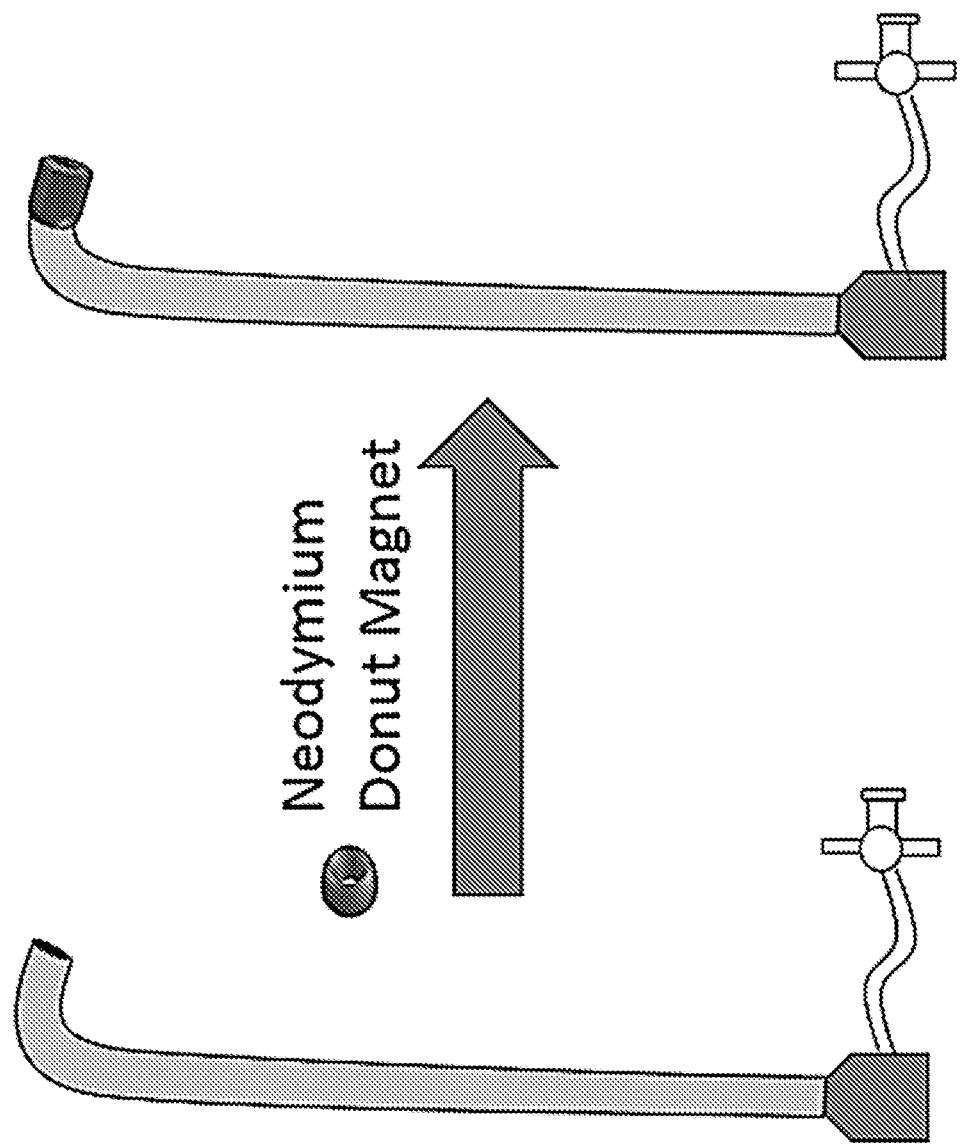
FIG. 14A illustrates an exemplary magnetically tipped vascular sheath that can help solve the challenge shown in FIGS. 13A and 13B.
Figure 14B:
FIG. 14B illustrates another exemplary magnetically tipped vascular sheath.

FIGS. 14A and 14B illustrate exemplary magnetic guidewire catheters/sheaths that can help solve the challenge shown in FIGS. 13A and 13B. The magnetic guidewire sheath can include a magnet (e.g., a neodymium magnet) coupled to a distal tip of the sheath, as shown in the examples of FIGS. 14A and 14B. The magnet can have an annular shape (e.g., toroid, donut shaped, washer shaped, etc.), as illustrated, that encircles the distal opening of the sheath. The magnet can comprise a permanent magnet. In other embodiments, the magnet can comprise an electromagnet that is coupled to a remote power source, and capable of being selectively energized and de-energized.

Figures 15A, 15B:
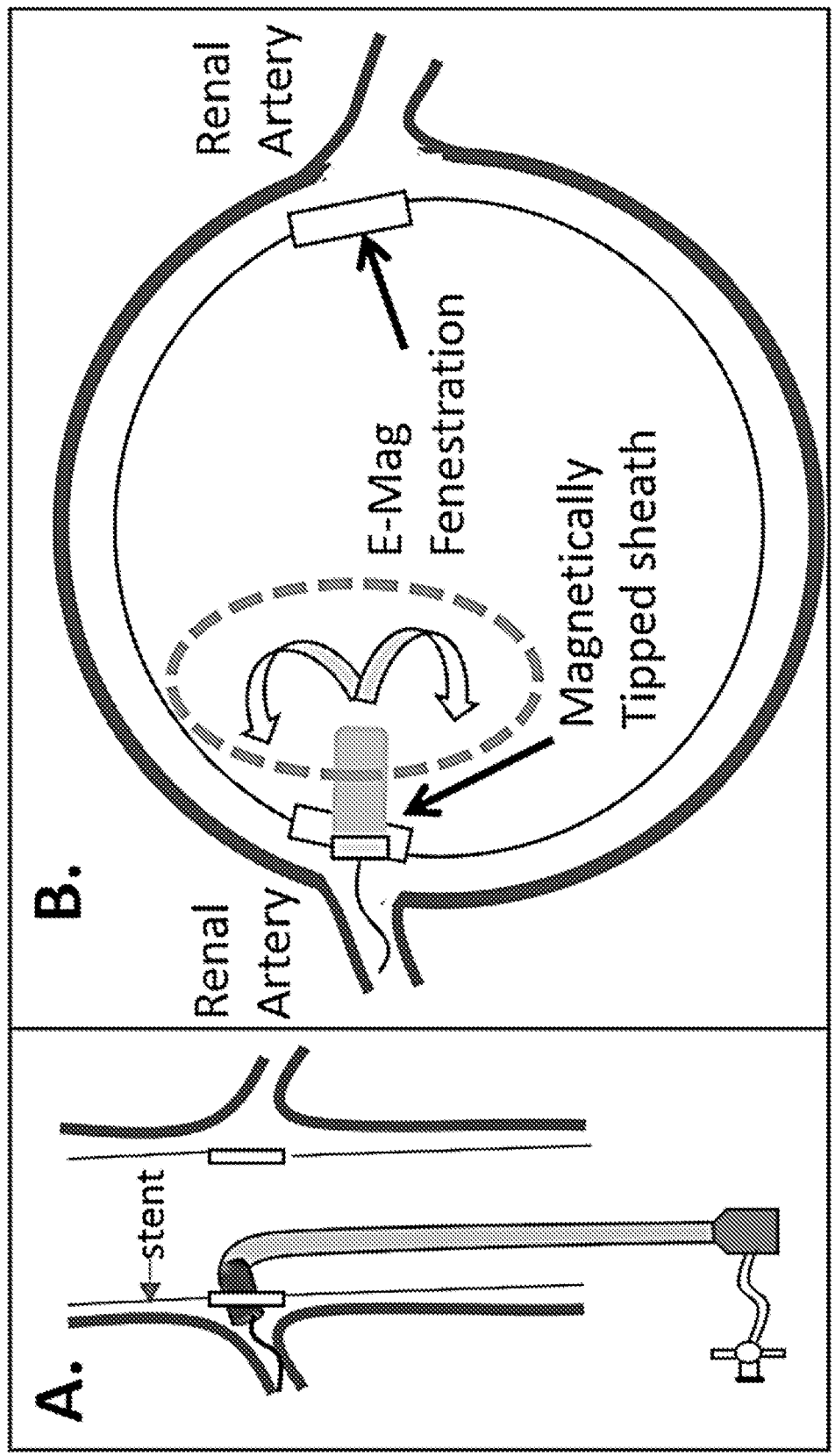
FIGS. 15A and 15B illustrate a magnetically tipped sheath, similar to those of FIGS. 14A and 14B, in an exemplary method.

FIGS. 15A and 15B illustrate a magnetically tipped sheath such as those of FIG. 14A or 14B in an exemplary method. In FIG. 15A, the magnetic tip of the sheath engages a fenestration opening of an aortic stent using magnetic attraction. The fenestration opening can include a wire coil around the fenestration, as disclosed herein. The probing wire can then be advanced from the sheath into the renal branch artery. FIG. 15B illustrates how the magnetic coupling between the sheath tip and the fenestration allows the sheath to pivot or rotate about the magnetic junction without losing the magnetic connection, which can provide a more desirable angle to better access the posteriorly angled renal artery with a probing wire and avoid dislodgement.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Characteristics, materials, and other features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of these claims.

The invention claimed is:

1. A method comprising:
   positioning a first tubular device within a blood vessel of a patient, the first tubular device comprising a tubular graft or stent having a main body and defining a plurality of openings in a sidewall of the main body, the first tubular device including a first electromagnetic coil positioned around a first opening of the plurality of openings in the sidewall of the first tubular device and a second electromagnetic coil positioned around a second opening of the plurality of openings in the sidewall of the first tubular device;
   positioning a second device within the first tubular device adjacent to the first opening in the first tubular device, the second device comprising a magnetic tip; and
   activating the first electromagnetic coil by causing electrical current to flow through the first electromagnetic coil of the first tubular device to create a magnetic field that draws the magnetic tip of the second device through the first tubular device to the first opening in the first tubular device;
   deactivating the first electromagnetic coil so that the first electromagnetic coil no longer creates a magnetic field;
   positioning a third device within the first tubular device adjacent to the second opening in the first tubular device, the third device comprising a magnetic tip;
   activating the second electromagnetic coil by causing electrical current to flow through the second electromagnetic coil to create a magnetic field that draws the magnetic tip of the third device through the first tubular device to the second opening in the first tubular device; and
   deactivating the second electromagnetic coil so that the second electromagnetic coil no longer creates a magnetic field.

2. The method of claim 1, wherein the first opening in the first tubular device comprises a fenestration in the sidewall of the first tubular device.

3. The method of claim 1, wherein positioning the second device within the first tubular device adjacent to the first opening in the first tubular device comprises positioning a transluminal device within the first tubular device.

4. The method of claim 1, wherein the second device is a guidewire, and causing electrical current to flow through the first electromagnetic coil creates a magnetic field that draws the guidewire through the first opening in the first tubular device and into an adjacent anatomical structure.

5. The method of claim 1, further comprising delivering a fourth device through the first opening in the first tubular device over or through the second device.

6. The method of claim 1, wherein the first electromagnetic coil is wound around a tubular gate portion extending outwardly from the first opening of the first tubular device.

7. The method of claim 1, further comprising a nosecone attached to the first tubular device for delivery through vasculature, the nosecone containing an electrical power source that is electrically coupled to the first electromagnetic coil and to the second electromagnetic coil by wires extending from the power source in the nosecone to the first electromagnetic coil and to the second electromagnetic coil; and
   wherein the method further comprises detaching the wires from the nosecone and withdrawing the nosecone from the patient.

8. The method of claim 1, wherein the second device and the third device are guidewires.

9. An apparatus comprising:
a tubular main body configured to be implanted within a patient;
a fenestration in a wall of the tubular main body;
the tubular main body comprising a tubular gate portion extending outwardly from the tubular main body, the tubular gate portion being in fluid communication with the tubular main body through the fenestration and shaped and sized to receive a separately delivered stented branch through the tubular gate portion; and
an electromagnetic coil wound on the tubular gate portion and positioned around the fenestration, the electromagnetic coil being switchable between an activated state and a deactivated state, the electromagnetic coil being operable to generate a magnetic field when electrical current flows through the electromagnetic coil in the activated state such that the electromagnetic coil is operable to magnetically guide another device to or through the fenestration; and
a nosecone attached to the tubular main body for delivery through vasculature, and wherein the nosecone contains an electrical power source that is electrically coupled to the electromagnetic coil.

* * * * *